United States Patent [19]

Loper et al.

[11] Patent Number: 4,797,284

[45] Date of Patent: Jan. 10, 1989

[54] TRANSDERMAL DRUG DELIVERY SYSTEM

[75] Inventors: Alice E. Loper, Lederach, Pa.; Anup K. Majumdar, Eatontown, N.J.

[73] Assignee: Merck & Co., Inc., Rahway, N.J.

[21] Appl. No.: 838,852

[22] Filed: Mar. 12, 1986

[51] Int. Cl.⁴ .................................................. A61F 13/00
[52] U.S. Cl. ...................................... 424/449; 424/448
[58] Field of Search ............................................ 424/449

[56] References Cited

U.S. PATENT DOCUMENTS

| | | | |
|---|---|---|---|
| 3,598,122 | 8/1971 | Zaffaroni | 424/449 |
| 3,716,795 | 1/1973 | Higuchi et al. | 424/449 |
| 3,854,480 | 12/1974 | Zaffaroni | 424/449 |
| 3,993,072 | 11/1976 | Zaffaroni | 424/449 |
| 4,060,084 | 11/1977 | Chandrasekaran | 424/449 |
| 4,144,317 | 3/1979 | Higuchi et al. | 424/449 |
| 4,286,592 | 9/1981 | Chandrasekaran | 424/449 |
| 4,336,243 | 6/1982 | Sanvordeker et al. | 424/449 |
| 4,460,372 | 7/1984 | Campbell et al. | 424/449 |
| 4,568,343 | 2/1986 | Leeper et al. | 424/449 |
| 4,605,548 | 8/1986 | Ushiyama et al. | 424/449 |
| 4,753,995 | 3/1986 | Chen et al. | 424/449 |

Primary Examiner—Gerorge F. Lesmes
Assistant Examiner—L. R. Horne
Attorney, Agent, or Firm—Alice O. Robertson; Michael C. Sudol

[57] ABSTRACT

A multilaminate transdermal drug delivery system containing only dissolved drug in the drug reservoir is described. The delivery system comprises a backing layer, a reservoir layer and a membrane layer, wherein the drug in the reservoir is completely dissolved and the control of delivery is effected by the joint action of reservoir and membrane.

12 Claims, 2 Drawing Sheets

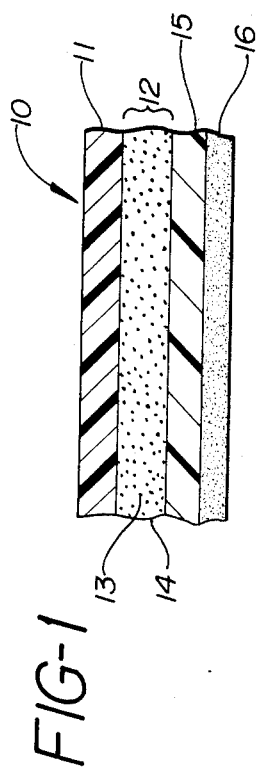
FIG-1
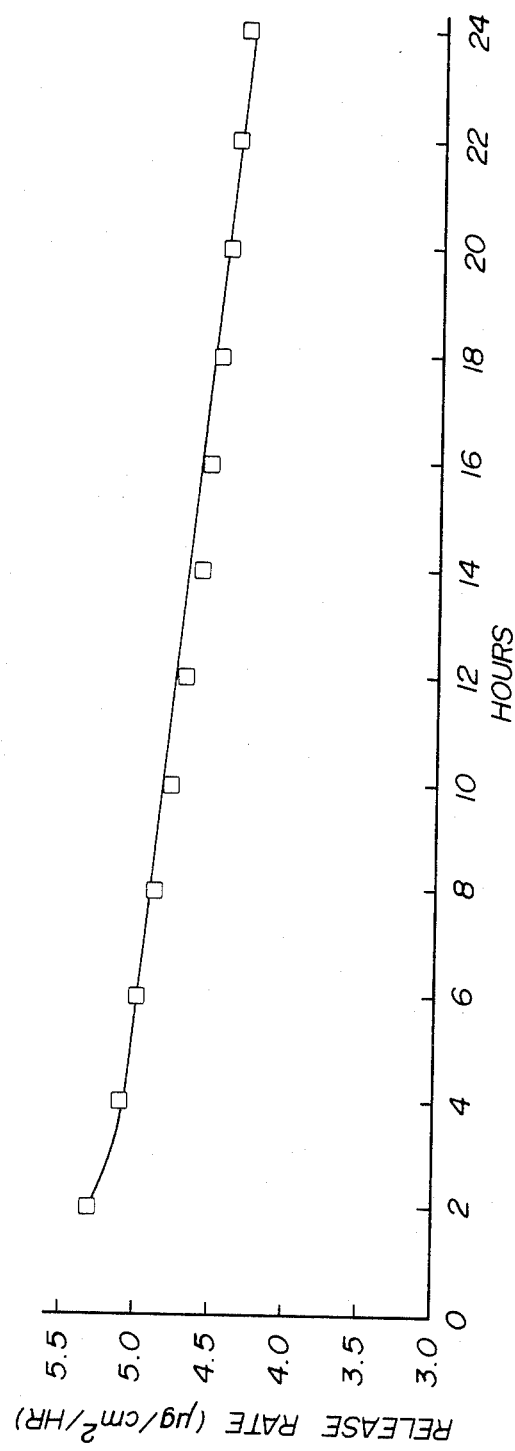
FIG-3 SYSTEM OF EXAMPLE II.

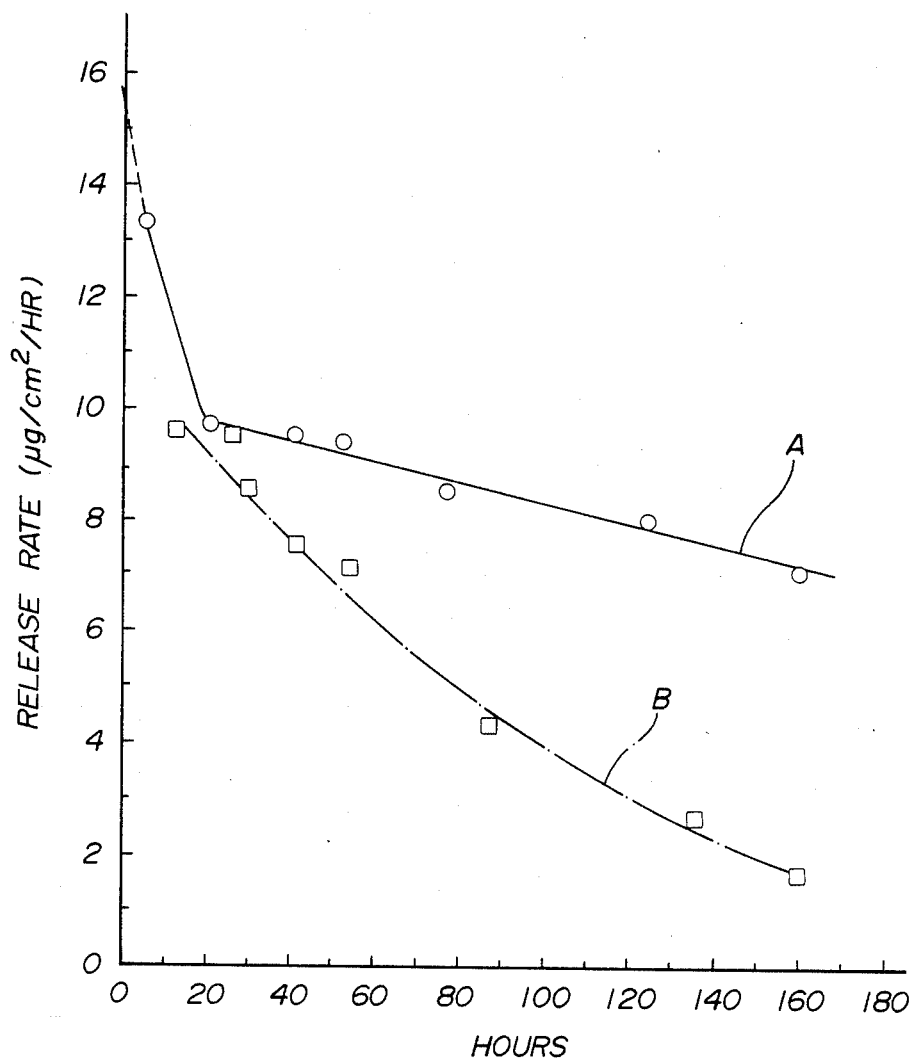
FIG-2 SYSTEM OF EXAMPLE I.

TRANSDERMAL DRUG DELIVERY SYSTEM

The invention is concerned with a transdermal drug delivery system and most particularly with a system in which the drug in the drug reservoir is in a totally dissolved state.

BACKGROUND OF THE INVENTION

In recent years there have been provided devices or bandages for delivery of drugs to and through the skin or mucosa of the wearer as a means of providing continuous, controlled administration to the circulation thereby avoiding the uncertainties of oral administration and the inconvenience of administration by injection. Some of the best known applications of such transdermal administrations are the administration of nitroglycerine and of scopolamine.

Much patent literature has appeared directed to various devices for transdermal administration. Most of these are directed to various systems or structures and materials for improved delivery. Many of these systems have been developed as a method for delivering steroidal drugs and some of the devices employing such systems have been adapted for application with other drugs. When it is attempted to employ these developed systems with other drugs, problems have been encountered which have demonstrated that known systems are not necessarily applicable to all types of drugs.

Generally, the structure of a transdermal bandage or device consists of (a) a transdermal delivery system comprising an impermeable backing, a drug-containing reservoir, a rate-controlling membrane on the side to be ultimately proximate to the skin of the patient and (b) a means of attaching the system to the dermal surface. In the known systems, the reservoir, the source of supply for the drug, whether a single solid unit, a walled unit or a unit employing drug containing micro-capsules within the reservoir structure, contains the drug partly in particulate form and partly in solution i.e., contains drug in excess of its saturation solubility. During use, the drug in solution migrates to the permeable membrane surface, passes through the membrane and onto the skin for absorption. As the dissolved drug passes through the membrane some of the undissolved drug dissolves and there is, until the supply of undissolved drug is exhausted, a mixture of both dissolved and undissolved drug in the reservoir. The presence of dissolved and undissolved drug is considered necessary to provide for the near zero order rate of delivery, zero order being the rate of delivery which is constant or independent of time. It has been found, however, that when certain drugs such as, for example, timolol, are employed in a unitary solid reservoir of dissolved and undissolved drug, the dissolved drug often slowly crystallizes subsequent to fabrication. When crystallization occurs especially when accompanied by the formation of large crystals, dissolution, rather than diffusion, becomes the rate limiting process in drug release, thereby impairing the predictability of release rate and consequently the desired control in the administration of the drug. Such bandages would not be suitable for use in controlled therapy. Even if crystal size may be small enough to render the bandage utilizable, the waiting period necessary to complete the crystal formation can result in undesirable delay in manufacture. Moreover, at least in some cases, crystallization of a less preferred crystalline structure or separation of an amorphous form may occur which also may impair rate control. Thus, it is evident that for a transdermal bandage of certain drugs, the reservoir system containing both solid and dissolved drug has practical limitations in providing a less predictable delivery system.

SUMMARY OF THE INVENTION

According to the present invention it has been discovered that by a proper selection of reservoir medium and rate controlling membrane, the drug may be supplied in the reservoir in a completely dissolved form and still provide a bandage exhibiting substantially constant delivery rate during the time required to accomplish the desired therapy. Thus, there can be provided a transdermal system suitable for use for all drugs but especially useful for those drugs whose properties render them unsuitable in the manufacture of bandages employing conventional delivery systems in which the drug is supplied as a mixture of undissolved and dissolved drug.

DETAILED DESCRIPTION OF THE INVENTION

The invention resides in the discovery that a substantially constant release of drug may be achieved from a reservoir in which the drug is completely in the dissolved form in a relatively simple transdermal delivery system of an impermeable backing layer, a drug reservoir layer, and a rate controlling membrane layer. A release profile indicating that a substantially constant release of drug for a period of time sufficient to be effectively utilized for therapeutic purposes was discovered and found to rest on certain relationships among diffusion coefficient of the drug in the reservoir, the reservoir thickness, the diffusion coefficient of the drug in the membrane, the membrane thickness, and the partition coefficient between the membrane and the reservoir.

According to the present invention there is provided a transdermal system for administering drug for an extended period comprising (a) a backing layer substantially impermeable to the drug and forming the top or outer surface of a bandage employing the delivery system, (b) a reservoir layer comprising dissolved drug in a continuous matrix of carrier, and (c) a membrane layer comprising a structure exhibiting some rate controlling property, wherein the following relationships are satisfied simultaneously:

$$\frac{h/KD_m}{x_{max}/D_r} \geq \frac{(1 - \beta\alpha)}{\beta\alpha} \quad (1)$$

and $$\frac{(x_{max})^2}{(TD_r)} \geq \frac{\beta\alpha}{(2\alpha - \beta\alpha - \beta\alpha^2)} \left[ (1 - \alpha) + \left\{ \frac{(1 - \alpha)(2 + 2\alpha - 3\beta\alpha - \beta\alpha^2)}{2 - \beta\alpha} \right\}^{\frac{1}{2}} \right] \quad (2)$$

and wherein
  h is membrane thickness
  K is partition coefficient of drug between membrane and reservoir
  $D_m$ is diffusion coefficient of drug in membrane
  $x_{max}$ is reservoir thickness
  $D_r$ is diffusion coefficient of drug in reservoir, T is the desired wear time of the bandage, α is a design parameter ranging from but not including 0 to but not including 1, and which represents the fractional drop in the theoretical flux from time zero to the end of the wear period T, β is a design parameter ranging from but not including 0 to and including 1, which allows adjustments to shape of release profile, initial concentration, $C_o$, fraction of total drug depleted from the reservoir, h and $x_{max}$; and ≧ signifies equal to or greater than.

By "membrane layer comprising a structure exhibiting some rate controlling property" is meant either a semipermeable membrane or a properly prepared microporous membrane through which rate control is obtained by the extent of diffusivity of the drug therein.

By the appropriate selection of reservoir matrix and membrane to satisfy the conditions, of Equations (1) and (2) as specified below, a substantially constant rate of release over a substantial part of the time period for therapy is effected by the joint control of the reservoir matrix and the membrane. The design parameter, α, is a function of the therapeutic index of the drug. For most drugs, the preferred range for α is from 0.01 to 0.67, when substantially constant rate of release is desired. For a drug with a narrow therapeutic index, α is preferably lower than 0.3 with a preferred range from 0.3 down to 0.01.

For a system of optimal properties, i.e., one which utilizes the thinnest membrane, the lowest initial concentration, $C_0$, in the reservoir matrix, and tolerates the largest partition coefficient K to achieve the desired delivery, the value of design parameter, β, is 1, while α ranges from 0.01 to 0.67, preferably from 0.01 to 0.3.

For a suboptimal system, i.e., one that is less efficient in terms of thinness of the membrane to be utilized, of tolerance for K or of the least concentration of drug in the reservoir to achieve the desired delivery, the value of design parameter β is less than 1, while α remains in the range 0.01 to 0.67, preferably from 0.01 to 0.3. Typically, a suboptimal bandage design for a given delivery profile will result in a higher value for $$\frac{h/KD_m}{x_{max}/D_r}$$

and a lower value for $$\frac{(x_{max})^2}{TD_r}$$

than a corresponding optimal patch design.

Optimal conditions may not be the most desirable. For example, the efficiency may be so great that such a thin membrane is called for that from practical considerations such as handling during manufacture it would be less desirable. A suboptimal system uses a thinner reservoir than that called for by a corresponding optimal design and is desirable when a high fractional depletion of drug from the reservoir is sought. A suboptimal sys system is also desirable when the optimal system would call for a reservoir which would be so thick that it would be impractical for wearability.

The present invention is not limited to any particular class of drugs. The drug to be employed should have a solubility of about 0.1 percent or greater in the reservoir material. It is especially useful for the more "potent" drugs, i.e., those to be administered at a daily dose of about 20 mg or less. Thus, classes of drugs for which the present invention is most useful include, tranquilizers, analgesics, antimigraine drugs, CNS active drugs, antihistamines, dopanergic drugs, anti-cholinergics, β-blockers, calcium entry blockers, anti-anginal drugs, and other cardiovascular drugs but are not limited thereto.

BRIEF DESCRIPTION OF THE DRAWINGS

In the drawings:

FIG. 1 is a schematic sectional view of a transdermal delivery system;

FIG. 2 is a graph of timolol release rate with time in the timolol solution reservoir system of Example I;

FIG. 3 is a graph of the noxazinol solution reservoir system of Example II.

DESCRIPTION OF EMBODIMENTS OF THE INVENTION

FIG. 1 illustrates the basic and preferred structure of a transdermal bandage incorporating the transdermal delivery system, generally designated 10. The components are the backing layer 11, drug reservoir layer 12 consisting of drug 13 homogeneously distributed as a molecular solution in a continuous matrix 14, a membrane layer 15 coextensive with the drug reservoir layer and along the surface opposite that occupied by the backing layer and optionally, but preferably, an adhesive layer 16 along the opposite surface of the membrane layer as a means for affixing the bandage to the skin.

The backing member is impermeable to the drug and prevents back diffusion of the drug into the environment. The backing member may be of any of a number of impermeable materials taught in the transdermal bandage art. Suitable backing materials include polyethylene, polypropylene, polycarbonate, polyester, polyethylene terephthalate (PET), metal foils, and the like.

The matrix may be solid, or if a wall structure is employed for the reservoir, it may be a gel. A solid reservoir is preferred.

Materials for the continuous matrix of the reservoir layer, if solid, and for the membrane layer may be selected from a number of polymers. A particular polymer is not limited as being suitable only for the reservoir matrix or for membrane layer. The selection is dependent on the solubility and diffusivity of the particular drug in each polymer and the time during which an approximately constant release rate is sought. Suitable polymers for a solid matrix include silicones, acrylic adhesive resins, ethylene vinyl acetate copolymers, plasticized polyvinyl acetate/polyvinyl chloride resins, plasticized hydrolyzed polyvinyl alcohol, rubber-based adhesives such as polyisobutylenes extended with a solvent such as mineral oil, plasticized polyvinyl chloride, polyethylene glycols and polypropylene glycols of varying molecular weights, and cellulose esters. If the polymer selected is one which has adhesive properties it may serve the dual function of a rate controlling membrane of the transdermal system and an affixing adhesive when the transdermal system is part of a bandage. Hydrogel polymers which are useful as matrix polymers include poly(hydroxyalkyl methacrylate)s of which poly-(2-hydroxyethyl methacrylate), poly(glyceryl methacrylate) and poly(hydroxypropyl methacrylate) are well-known and identified in the literature as (P-HEMA), (P-GMA) and (P-(HPMA), respectively.

Other hydrogel polymers include poly(acrylamide), poly(methacrylamide), poly(N-vinyl-2-pyrrolidine), and poly(vinyl alcohol), hydroxypropyl guar, high molecular weight polypropylene glycol or polyethylene glycol, and the like.

Polymers which may be employed where the drug reservoir is in a walled structure include the foregoing hydrogel polymers extended with solvents such as propylene glycol, glycerine, low molecular weight polyethylene glycol and the like.

The membrane which has rate-controlling properties may be a solid semi-permeable film of the materials above described but may also be a microporous membrane of material such as microporous polypropylene, polyethylene or polycarbonate. Other substantially impermeable materials such as those useful as backing materials may be made microporous by treatment known to those skilled in the art. If a microporous membrane is employed the pores must be at least ten times the molecular diameter of the drug and the pores must be filled with material which satisfies the requirements for K and $D_m$. The drug should have essentially no solubility in or permeability through the material from which the microporous membrane is prepared. If a microporous membrane is used as the membrane in the system, Equation 1 should be modified to be $$\frac{\tau h/EK'D_{m'}}{x_{max}/D_r} \geq \frac{(1-\beta\alpha)}{\beta\alpha} \quad (1A)$$

wherein $\tau$ is the tortuosity of the diffusion path through the membrane

E is the fractional porosity of the membrane $K'$ is the drug partition coefficient between material in the micropores and the reservoir material $D_{m'}$ is drug diffusion coefficient in the material in the micropores of the membrane, and all other terms are as previously defined. For substantially constant release, $\alpha$ ranges from 0.01 to 0.67 preferably from 0.01 to 0.3. If an optimal system is sought, then $\beta$ is 1. For a non-optimal system, $\alpha$ is as defined and $\beta$ is less than 1 and greater than zero. Equation 2 must be satisfied simultaneously with Equation 1A for both optimal and non-optimal bandages.

As noted previously, the membrane may be of material which has adhesive properties thereby serving as a means for affixing the system to skin or other biological membrane. Alternatively, a layer of adhesive may be employed as an affixing means. If an adhesive is employed in addition to a semipermeable membrane, the nature of the adhesive must be such that there is substantially no solubility of the drug in the adhesive and further that the adhesive be of such permeability and porosity as to exhibit no deterrent to the movement of the drug from the membrane to the dermal or mucosal surface. Suitable adhesives include silicone rubber, pressure sensitive acrylate resins, polyisobutylenes, polyisobutylenes extended with suitable solvents such as mineral oil, as well as other medical adhesives such as, for example, those noted in the chapter by Gross et al on "Medical and Biological Adhesives" in Handbook of Adhesives edited by I. Skeist, Van Nostrand Reinhold, New York.

In carrying out the preparation of the drug delivery systems, the initial step is the determination of the diffusion coefficient of the drug in the reservoir, $D_r$, the diffusion coefficient of the drug in the membrane, $D_m$ or $D_{m'}$, and the partition coefficient, K or $K'$. These determinations are made employing standard methods familiar to the skilled artisan and are briefly summarized below.

When a solid reservoir is employed, the diffusion coefficient of the drug in the reservoir, $D_r$, is determined by first dissolving the drug to be used in a solution of matrix-forming polymer at a concentration below the saturation solubility of the drug in the polymer solution, and then coating the solution and allowing the coating to dry or curing the coating to form a drug bearing film. The coating may be made on a releasable surface so that a free film is employed in the diffusion coefficient determination or may be made on an impermeable backing material in which case the film with backing is employed in making the determination. The film is then mounted so that the surface of the film contacts a stirred receptor solution which serves as a sink for the drug and which does not swell or dissolve the film. The receptor solution, which is maintained at a constant temperature, preferably 32° C., is sampled at appropriate intervals and quantitative determination of drug concentration made by HPLC (high pressure liquid chromatography) with UV detection or by other suitable means based on the physical-chemical characteristics of the drug. The value for $D_r$ is then determined by a nonlinear regression fit of observed data to either the earlier time or the late time approximation as is appropriate for drug release from a continuous matrix containing only dissolved drug as discussed in Baker et al, "Controlled Release: Mechanisms and Rates" in *Advances in Experimental Medicine and Biology*, Vol 47, page 41, Eds. Tanquary et al, Plenum Press, N.Y., 1974. The experimental determination of diffusivities of molecular solutes in liquid and gel media and theoretical calculations of diffusion coefficients are well known. Bird et al., "Diffusivity and the Mechanism of Mass Transport" in *Transport Phenomena*, pp. 495–515, John Wiley & Sons, New York, N.Y., 1960.

The diffusion coefficient of drug in the membrane, $D_m$ or $D_{m'}$, is determined by mounting the membrane between two chambers of a side-by-side diffusion cell. A determined amount of drug in solution (donor phase) is placed in one chamber and a receptor solvent in the other, into which the drug diffuses and in which it will remain substantially below its saturation solubility (receptor phase). The cells are stirred while maintained in a constant temperature bath, preferably at 32° C. The receptor phase is sampled from time to time and assayed for drug, and steady state flux through the membrane calculated. $K_m$, the partition coefficient between the donor solution and membrane, is determined by equilibrating a known volume of donor solution at 32° C., then assaying the solution for change in drug concentration to determine partitioning between membrane and donor. The diffusion coefficient of the drug in the membrane is calculated from the steady state Fick's law equation, which for semi-permeable membrane is $$J_{ss} = K_m C D_m / h$$

and for microporous membrane is $$J_{ss} = \frac{EK_m C D_{m'}}{\tau h}$$

where $J_{ss}$ is steady state flux (delivery rate) through the membrane, C is the drug concentration in the donor phase, and the other symbols have the same significance as in the prior equations.

The partition coefficient for the completed delivery system, K or K', may be determined by alternative methods. When one component of the patch such as the materials in the micropores of a microporous membrane is a liquid and the other component is a solid, the partition coefficient, K', may be determined employing a method analogous to a conventional liquid-liquid partitioning relationship as described on pages 138-139 of *Chemical Equilibrium* by A. J. Bard, Harper and Row, New York, N.Y., 1966. A known volume of liquid is equilibrated with a known volume or weight of solid which contains a known concentration of drug, and the liquid is assayed to determine drug concentration. The partition coefficient is the ratio between concentration in the liquid and final concentration in the solid.

When both reservoir and membrane are solids, K can be indirectly estimated by preparing a prototype system using reservoir material with known $D_r$ and $C_o$, and membrane material with known $D_m$. For this purpose, the thickness, $x_{max}$, selected for the reservoir material, and the thickness, h, selected for the membrane material are arbitrary, the selection being consistent with ease of handling. The materials of the prototype system then are mounted in a diffusion cell as used to determine $D_r$ and samplings made from the receptor phase at a time close to zero time and assayed for drug. This provides an estimate of initial flux, $J_o$, which can be used to calculate K from the relationship $J_o = KC_oD_m/h$.

Alternatively, the entire drug release profile from the prototype system can be generated, and K determined by statistically fitting experimental observations to the differential equations which describe release rate from the entire system. The statistical fitting with this model requires selecting several initial estimates for K. These initial estimates, together with known parameters, $C_o$, $D_r$, $D_m$, and the arbitrary values for $x_{max}$ and h, can be used to simulate release profiles by numerical solution of differential equations which describe this system. The sum of squared differences between each simulation and the experimental observations are calculated, and a suitable search technique (such as a Simplex search) is used to arrive at the value of K which provides the minimum differences between observed values and simulated values. (This is analogous to the use of nonlinear regression techniques to fit observed data to the integrated form of equations.)

After determining the partition coefficient (K) and the diffusion coefficient for the particular drug in the materials selected for the system, desired values for the design parameters $\alpha$ and $\beta$ are chosen within the ranges previously set forth. After $\alpha$ and $\beta$ have been selected, reservoir thickness ($x_{max}$) is calculated from Equation 2. Then, membrane thickness (h) is calculated from either Equation 1 or 1A for semipermeable (solution) membrane or microporous membrane, respectively. The values for $\alpha$, $\beta$, $x_{max}$ and h must be such that Equations 1 or 1A and Equation 2 are satisfied simultaneously.

After $x_{max}$ and h are calculated for any system above described, drug concentration in the reservoir $C_o$, is calculated employing Fick's law, using for semipermeable membrane $$J_o = \frac{KC_oD_m}{h}$$

and for microporous membrane $$J_o = \frac{EK'C_oD_m'}{\tau h}$$

to obtain the desired concentration of the drug in the reservoir needed for the desired magnitude of drug delivery. $J_o$ is initial flux from the system which is chosen so that $J_o$ and $J_t$ are consistent with the therapy for the drug of interest wherein $J_t$ is flux at the end of the wear period.

The transdermal bandage or drug delivery system may then be prepared employing the materials and dimensions determined above. A solution of drug and reservoir matrix material is coated onto an impermeable backing. The coating must be of suitable "wet" film thickness to provide for the desired final reservoir thickness. Thereafter, the solvent is removed from the film by drying to obtain a drug reservoir matrix as a film on backing material. The reservoir matrix may be coated onto the backing material using other techniques such as hot melt deposition, extrusion and the like. Following this step, a membrane of predetermined thickness is laminated onto the reservoir layer to obtain the desired transdermal delivery system. If desired, the membrane layer may be coated with an adhesive to obtain a bandage provided that the adhesive selected is one that provides a free flow of the drug. Alternatively other fastening means may be employed.

When the reservoir matrix is a gel, the transdermal delivery system may be produced in a similar manner, or in a manner similar to a liquid in which case an appropriate solution is metered into an appropriate envelope or walled container as reservoir.

When drug release rate versus time for the transdermal delivery system is determined by a suitable in vitro diffusion method, such as that employed to determine $D_r$, the desired therapeutic dosage of drug may be delivered at a substantially constant delivery rate for a substantial portion of the time required for said delivery.

When the transdermal bandage is one employing a microporous membrane instead of a semipermeable membrane, the drug delivery system is prepared in a similar manner except that Equations 1A and 2 must be satisfied simultaneously. The microporous membrane first must be primed to provide some rate controlling properties, and the diffusivity determined on the primed microporous membrane. By "primed microporous membrane" is meant that the pores have been prepared or treated for diffusion control. The microporous membrane which may be a commercially available microporous membrane or one prepared by known methods, may be primed by known methods. One method which may be employed to prepare a microporous membrane is to soak the membrane in a solvent which will be the medium for transport of the drug, which solvent then fills the pores of the membrane. When the solvent desired in the pores does not wet the particular microporous membrane, a stepwise procedure may be required. Thus, for example, if it is desired to have propylene glycol in the pores of a microporous polypropylene membrane, it would be necessary to wet the pores by first soaking the membrane with isopropanol, then dipping the membrane in a 50:50 propylene glycol/isopropanol mixture, thereafter in a mixture having a higher concentration of propylene glycol, and repeating the procedure with increasing concentration of propylene glycol until the membrane is wetted with 100 percent propylene glycol.

The bandages employing the system of the present invention have numerous advantages. They show stability in storage, i.e., there is substantially no tendency for the drug to crystallize out during storage or manufacture, thereby eliminating an annealing period after the step of coating with the reservoir matrix, and since the drug is always in solution they may be prepared without carrier materials to retain the drug homogeneously dispersed.

The following examples illustrate the invention but are not to be construed as limiting.

EXAMPLE I

In the preparation of a delivery system for the drug timolol (a $\beta$-adrenoreceptor blocking agent for the treatment of hypertension), timolol was employed in the free base form, an acrylate was selected for the reservoir matrix, ethylene vinyl acetate for the membrane and polyethylene for the backing.

Initially, $D_r$ was determined for timolol in a commercially available acrylate film-forming material, a 30 percent weight/weight (w/w) vinyl acetate-acrylate copolymer in 53:11:36 ethyl acetate:toluene:ethanol solvent (Gelva® RA-737 multipolymer solution obtained from Monsanto) in the manner previously described. $D_r$ was determined to be $1.58 \times 10^{-6}$ cm$^2$/hour. $D_m$ was then determined using 7.5 percent ethylene vinyl acetate copolymer film (PE-75 from Pierson Industries) and found to be $2.85 \times 10^{-6}$ cm$^2$/hour. K value was obtained by carrying out diffusion studies with the membrane material and the reservoir material, employing a membrane and reservoir film of arbitrarily selected thickness, and measuring flux, and determining K by statistically fitting differential equations describing the model to the observed drug release profile from the system. It was found to be approximately 0.064.

For timolol, the desired drop in flux, $\alpha$, was set at 0.5, and since it was desired to design an optimal system (i.e., minimum h and $C_o$), $\beta$ was set equal to 1.0.

The desired thickness of the reservoir layer was determined from Equation 2, the membrane thickness was determined from Equation 1, and the desired $C_o$ was approximated from the relationship $$J_o = \frac{KC_oD_m}{h}$$

From $D_r$, $D_m$ and K obtained from preliminary experimental determinations, from h and $x_{max}$ and $C_o$ determined by calculation and the known desired time over which a determined amount of drug is to be administered, the drug delivery system then was prepared.

First the drug reservoir was prepared by dissolving 0.20 gram of anhydrous timolol base in 2.67 grams of the above-identified vinyl acetate-acrylate copolymer solution to obtain a final dry film concentration of 20 percent (w/w) timolol in acrylic resin solution. With a Gardner knife, the solution was cast to a wet film thickness of 0.072 centimeter onto a silicone coated paper release liner. The resulting coated film was allowed to dry at ambient temperature and pressure to obtain a solid reservoir. A polyethylene film of 0.005 centimeter thickness, said polyethylene film to be the backing, was laminated to the reservoir. The resulting reservoir contained 20 percent w/w anhydrous timolol base in an acrylic polymer film of 0.025 centimeter thickness.

The above-described ethylene vinyl acetate copolymer film of a thickness of 0.003175 centimeter then was laminated onto the reservoir after the release liner was removed from the reservoir. This film served as the membrane in the ultimate bandage.

The release rate of the drug from the delivery system was determined by mounting the system in a diffusion cell and measuring the rate of release into an isotonic phosphate buffer of pH 7.4. From the measured amount of release over time, the release rate was calculated. When the release rate was plotted against time, a profile identified as A in FIG. 2 was obtained. The drop in flux, $\alpha$, from time zero to 168 hours calculated from a curve fitted to the experimental values was approximately 0.54. This correlates with the desired figure of 0.5 for $\alpha$.

In a similar manner, a drug delivery system was prepared employing the same materials, employing the same values for $\alpha$ and $\beta$, but varying the thickness of the reservoir. A system was made having a final reservoir thickness of 0.0056 centimeter so that Equation 1 was satisfied but Equation 2 was not. When the amount of release was determined over time and the release rate was calculated over this period and plotted against time, a profile identified as B in FIG. 2 was obtained which shows a drop in flux considerably higher than the specified $\alpha = 0.50$.

The above determined release profiles show that when the reservoir thickness is 0.025 centimeter, the release rate becomes substantially constant after about the first forty hours (i.e., there is an approximately 25 percent drop between 48 and 168 hours) whereas when the reservoir thickness is 0.0056 centimeter, there is an undesirably large drop in the drug release rate over 48 to 168 hours.

EXAMPLE II

In the preparation of a delivery system for the drug noxazinol (1a,2,3,4a,5,6-hexahydro-9-hydroxy-4-propyl-4H-naphth[1,2-b]-1,4-oxazine, a dopamine agonist for the treatment of Parkinson's disease) the following procedure may be employed.

A 1.2 percent solution of drug is first prepared by dissolving, 0.12 gram of noxazinol as a free base in 9.88 grams of propylene glycol gelled with 2 percent hydroxypropyl guar (HP-60 Jaguar from Celanese). This serves as the dissolved drug reservoir.

A 3.4 centimeter × 3.4 centimeter impermeable polyester film, 0.005 centimeter thick, which serves as an impermeable backing member, is affixed along the perimeter on three sides with silicone adhesive to a 0.025 centimeter (10 mil) silicone elastomer (polysiloxane) film which serves as the membrane, to produce an envelope of approximately 9 square centimeters to confine the drug reservoir. A 0.657 cubic centimeter aliquot of drug reservoir material is metered thereinto, the fourth side sealed, and the material spread evenly to produce a reservoir of 0.073 centimeter thickness.

The release rate of the drug from the reservoir thus prepared may be determined in the manner described in Example I. The release profile of the delivery system would be as seen in FIG. 3 which would indicate a substantially constant release rate during the entire period.

What is claimed is:

1. A transdermal drug delivery system for administering a drug, chemically identifiable as (1a,2,3,4a,5,6-hexahydro-9-hydroxy-4-propyl-4H-naphth[1,2-b]-1,-oxazine, over an extended period comprising,
   (a) a backing layer substantially impermeable to the drug and forming the top or outer surface of a bandage employing the delivery system,
   (b) a resevoir layer comprising drug in a completely dissolved form in a continuous matrix of a carrier,
   (c) a membrane layer comprising a structure exhibiting some rate controlling property, wherein a substantially constant release rate is achieved over a substantial part of the wear period by the combined action of the reservoir layer and the membrane layer wherein:

$$\frac{h/KD_m}{x_{max}/D_r} \geq \frac{(1-\beta\alpha)}{\beta\alpha} \quad (1)$$

and $$\frac{(x_{max})^2}{(TD_r)} \geq \frac{\beta\alpha}{(2\alpha-\beta\alpha-\beta\alpha^2)}\left[(1-\alpha)+\left\{\frac{(1-\alpha)(2+2\alpha-3\beta\alpha-\beta\alpha^2)}{2-\beta\alpha}\right\}^{\frac{1}{2}}\right] \quad (2)$$

are satisfied simultaneously, and wherein:
   h is membrane thickness
   K is partition coefficient between membrane and reservoir
   $D_m$ is diffusion coefficient of drug in membrane
   $x_{max}$ is reservoir thickness
   $D_r$ is diffusion coefficient of drug in reservoir
   T is the desired wear time of the bandage,
   $\alpha$ is a design parameter ranging from but not including 0 to and including 0.67, and representing the fractional drop in the theoretical flux from time zero to the end of the wear period T and
   $\beta$ is a design parameter ranging from but not including 0 to and including 1, which allows adjustments to shape of release profile, initial concentration, $C_o$, fraction of total drug depleted from the reservoir, h and $x_{max}$; and
   $\geq$ signifies equal to or greater than.

2. A transdermal delivery system according to claim 1 wherein $\alpha$ is in the range of from and including 0.01 to and including 0.67.

3. A transdermal delivery system according to claim 1 wherein $\alpha$ is in the range of from and including 0.01 to and including 0.3.

4. A transdermal delivery system of claim 1 wherein the membrane layer is a semipermeable membrane.

5. A transdermal delivery system of claim 1 wherein the membrane layer is a primed microporous membrane and wherein $$\frac{\tau h/EK'D_{m'}}{x_{max}/D_r} \geq \frac{(1-\beta\alpha)}{\alpha}$$

$\tau$ is the tortuosity of the diffusion path through the membrane
h is membrane thickness
E is the fractional porosity of the membrane
K' is the drug partition coefficient between material in the micropores and the reservoir material
$D_{m'}$ is drug diffusion coefficient in the material in the micropores of the membrane
$x_{max}$ is reservoir thickness
$D_r$ is diffusion coefficient of drug in reservoir
$\alpha$ is a design parameter ranging from but not including 0 to and including 0.67, and representing the fractional drop in the theoretical flux from time zero to the end of the wear period
$\beta$ is a design parameter ranging from but not including 0 to and including 1, which allows adjustments to shape of release profile, initial concentration, $C_o$, fraction of total drug depleted from the reservoir h and $x_{max}$; and
$\geq$ signifies equal to or greater than.

6. A transdermal delivery system according to claim 5 wherein $\alpha$ ranges from and including 0.01 to and including 0.67.

7. A transdermal delivery system of claim 1 wherein the continuous matrix of the reservoir is solid.

8. A transdermal delivery system of claim 1 wherein the continuous matrix of the reservoir is a gel contained in a walled-container.

9. A transdermal delivery system comprising a system in accordance with claim 1 in which $\beta$ is 1.0.

10. A transdermal delivery system comprising a system in accordance with claim 5 in which $\beta$ is 1.0.

11. A transdermal delivery system comprising a system in accordance with claim 1 in which $\beta$ ranges from but not including 0 to but not including 1.

12. A transdermal delivery system comprising a system in accordance with claim 5 in which $\beta$ ranges from but not including 0 to but not including 1.

* * * * *